US011260364B2

(12) United States Patent
Jeong et al.

(10) Patent No.: US 11,260,364 B2
(45) Date of Patent: Mar. 1, 2022

(54) SUPER ABSORBENT POLYMER AND PREPARATION METHOD THEREOF

(71) Applicant: LG Chem, Ltd., Seoul (KR)

(72) Inventors: Ji Yoon Jeong, Daejeon (KR); Jun Kyu Kim, Daejeon (KR); Dae Woo Nam, Daejeon (KR); Tae Hwan Jang, Daejeon (KR); Bo Hyun Seong, Daejeon (KR); Yeon Woo Hong, Daejeon (KR); Su Jin Kim, Daejeon (KR); Seong Beom Heo, Daejeon (KR); Seon Jung Jung, Daejeon (KR); Hyung Ki Yoon, Daejeon (KR)

(73) Assignee: LG Chem, Ltd.

( * ) Notice: Subject to any disclaimer, the term of this patent is extended or adjusted under 35 U.S.C. 154(b) by 358 days.

(21) Appl. No.: 15/755,426

(22) PCT Filed: Dec. 28, 2016

(86) PCT No.: PCT/KR2016/015416
§ 371 (c)(1),
(2) Date: Feb. 26, 2018

(87) PCT Pub. No.: WO2018/110760
PCT Pub. Date: Jun. 21, 2018

(65) Prior Publication Data
US 2020/0122119 A1    Apr. 23, 2020

(30) Foreign Application Priority Data

Dec. 13, 2016    (KP) .................. 10-2016-0169388

(51) Int. Cl.
*B01J 20/26*        (2006.01)
*A61L 26/00*      (2006.01)
(Continued)

(52) U.S. Cl.
CPC ........... *B01J 20/267* (2013.01); *A61L 26/008* (2013.01); *A61L 26/0014* (2013.01);
(Continued)

(58) Field of Classification Search
CPC .... B01J 20/267; B01J 20/321; B01J 20/3293; B01J 20/28021; B01J 20/3231;
(Continued)

(56) References Cited

U.S. PATENT DOCUMENTS 4,973,632 A     11/1990   Nagasuna et al.
5,422,405 A *    6/1995   Dairoku ................. A61L 15/60
                                                                    525/384

(Continued)

FOREIGN PATENT DOCUMENTS

CN          1148395 A       4/1997
CN        101010364 A       8/2007
(Continued)

OTHER PUBLICATIONS

Third Party Observation for PCT/KR2016/015416 dated Apr. 9, 2019.
(Continued)

*Primary Examiner* — Andrew J. Oyer
(74) *Attorney, Agent, or Firm* — Lerner, David, Littenberg, Krumholz & Mentlik, LLP

(57) ABSTRACT

The super absorbent polymer according to the present invention has reduced 3-hour saline solution re-wet while having a high absorption rate and absorption against pulp, and thus can be used for hygienic materials such as diapers, thereby exhibiting excellent performance.

7 Claims, 4 Drawing Sheets

(51) Int. Cl.
*B01J 20/28* (2006.01)
*B01J 20/30* (2006.01)
*B01J 20/32* (2006.01)
*C08F 220/06* (2006.01)
*C08J 3/075* (2006.01)
*C08J 3/12* (2006.01)
*C08J 3/24* (2006.01)

(52) U.S. Cl.
CPC ..... *A61L 26/0052* (2013.01); *B01J 20/28021* (2013.01); *B01J 20/3085* (2013.01); *B01J 20/321* (2013.01); *B01J 20/3219* (2013.01); *B01J 20/3231* (2013.01); *B01J 20/3293* (2013.01); *C08F 220/06* (2013.01); *C08J 3/075* (2013.01); *C08J 3/12* (2013.01); *C08J 3/245* (2013.01); *C08J 2333/02* (2013.01)

(58) Field of Classification Search
CPC . B01J 20/3219; B01J 20/3085; A61L 26/008; A61L 26/0014; A61L 26/0052; C08F 220/06; C08J 2333/02; C08J 3/245; C08J 3/075; C08J 3/12
See application file for complete search history.

(56) References Cited

U.S. PATENT DOCUMENTS

| | | |
|---|---|---|
| 7,179,851 B2 | 2/2007 | Qin et al. |
| 7,396,584 B2 | 7/2008 | Azad et al. |
| 2003/0207997 A1 | 11/2003 | Mertens et al. |
| 2005/0137546 A1 | 6/2005 | Joy et al. |
| 2007/0203304 A1 | 8/2007 | Mitchell |
| 2007/0264489 A1* | 11/2007 | Sasabe ............... C08J 3/248 428/327 |
| 2010/0093949 A1 | 4/2010 | Herfert et al. |
| 2010/0261604 A1 | 10/2010 | Herfert et al. |
| 2010/0323885 A1 | 12/2010 | Herfert et al. |
| 2012/0091392 A1 | 4/2012 | Daniel et al. |
| 2015/0093575 A1 | 4/2015 | Naumann et al. |
| 2015/0097142 A1 | 4/2015 | Lindner et al. |
| 2016/0354757 A1 | 12/2016 | Lee et al. |
| 2016/0361703 A1 | 12/2016 | Jang et al. |
| 2017/0073478 A1 | 3/2017 | Joo et al. |
| 2017/0226248 A1 | 8/2017 | Kim et al. |

FOREIGN PATENT DOCUMENTS

| | | |
|---|---|---|
| CN | 102803316 A | 11/2012 |
| CN | 106133031 A | 11/2016 |
| EP | 0615736 A1 | 9/1994 |
| EP | 0644211 A1 | 3/1995 |
| EP | 0940148 A1 | 9/1999 |
| EP | 1169372 A1 | 1/2002 |
| EP | 1637105 A1 | 3/2006 |
| EP | 1730218 B1 | 12/2010 |
| EP | 2797566 B1 | 6/2019 |
| JP | H06015574 B2 | 3/1994 |
| JP | 2007530754 A | 11/2007 |
| JP | 4377432 B2 | 12/2009 |
| JP | 2010510045 A | 4/2010 |
| JP | 2010520948 A | 6/2010 |
| JP | 2011517703 A | 6/2011 |
| JP | 5153975 B2 | 2/2013 |
| KR | 930007272 B1 | 8/1993 |
| KR | 20140102264 A | 8/2014 |
| KR | 20150033629 A | 4/2015 |
| KR | 20160041826 A | 4/2016 |
| KR | 20160063956 A | 6/2016 |
| KR | 20160076422 A | 6/2016 |
| KR | 20160141666 A | 12/2016 |
| WO | 9527739 A1 | 10/1995 |
| WO | 2004020008 A1 | 3/2004 |
| WO | 2004096303 A2 | 11/2004 |
| WO | 2004099265 A1 | 11/2004 |
| WO | 2005092956 A1 | 10/2005 |
| WO | 2006025586 A1 | 3/2006 |

OTHER PUBLICATIONS

Buchholz, et al., Modern Superabsorbent Polymer Technology, 1998, vol. 152, pp. 199-201, New York: Wiley-vch.
Third Party Observation for EP16909742.5 submitted on Jan. 9, 2020, 4 pages.
Schwalm, "UV Coatings: Basics, Recent Developments and New Applications", Elsevier Science, Dec. 2006.
Odian, "Principles of Polymerization", Second Edition, A Wiley-Interscience Publication, 1981.
International Search Report for Application No. PCT/KR2016/015416 dated Sep. 11, 2017.
Chinese Search Report for Application No. CN 201680050601.0 dated Apr. 23, 2020, 2 pages.
Extended European Search Report including the Written Opinion for Application No. EP 16909742.5 dated Nov. 15, 2019, 14 pages.

* cited by examiner

[FIG. 1]
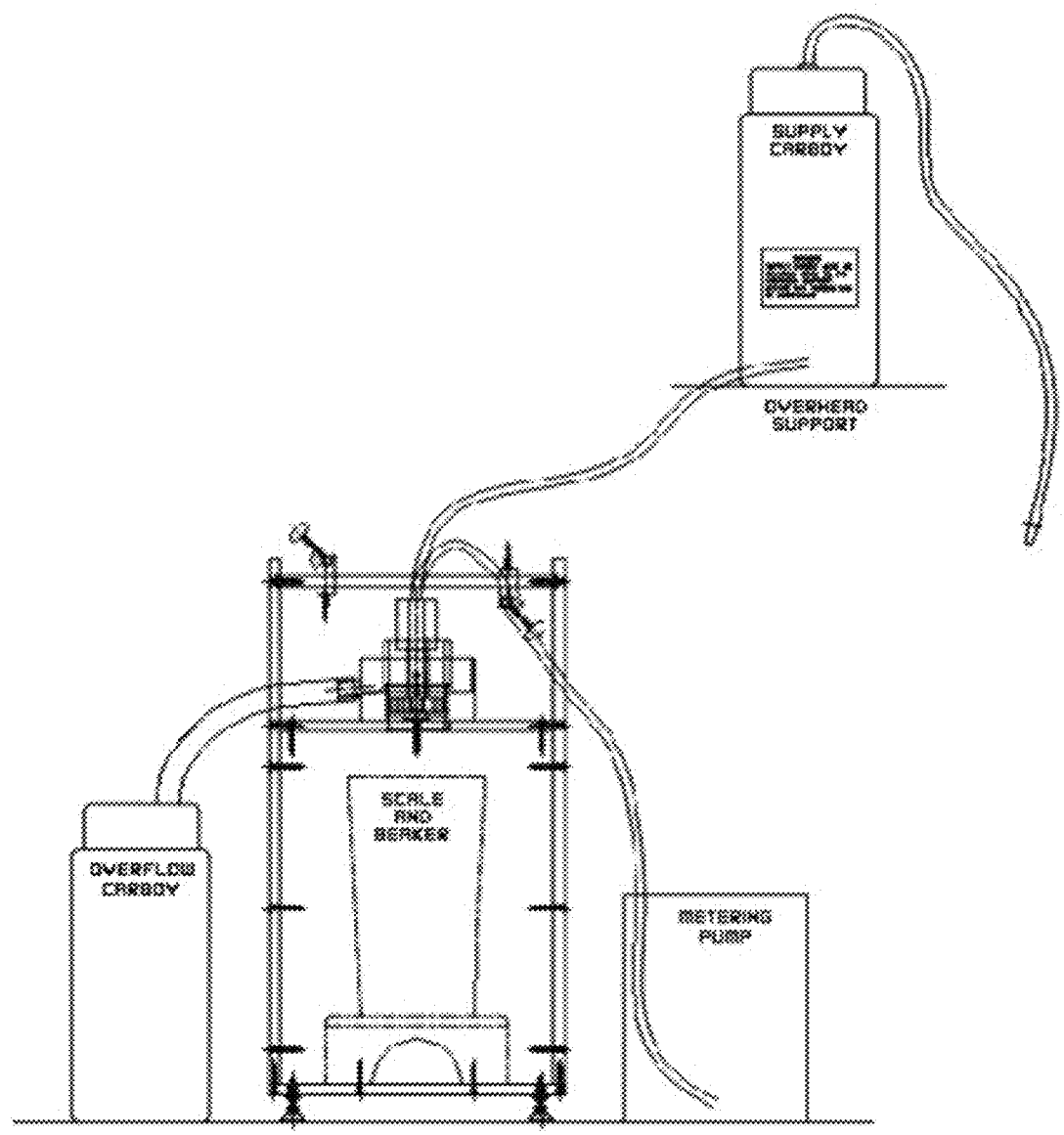

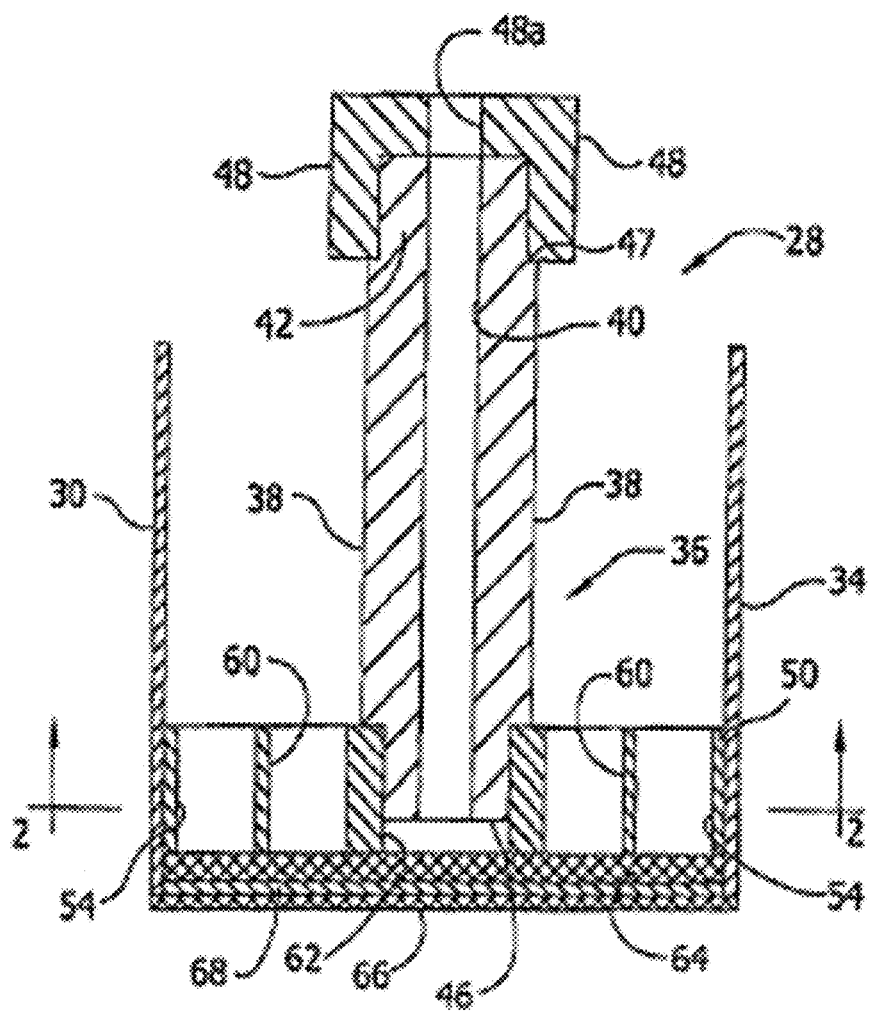
[FIG. 2]

[FIG. 3]
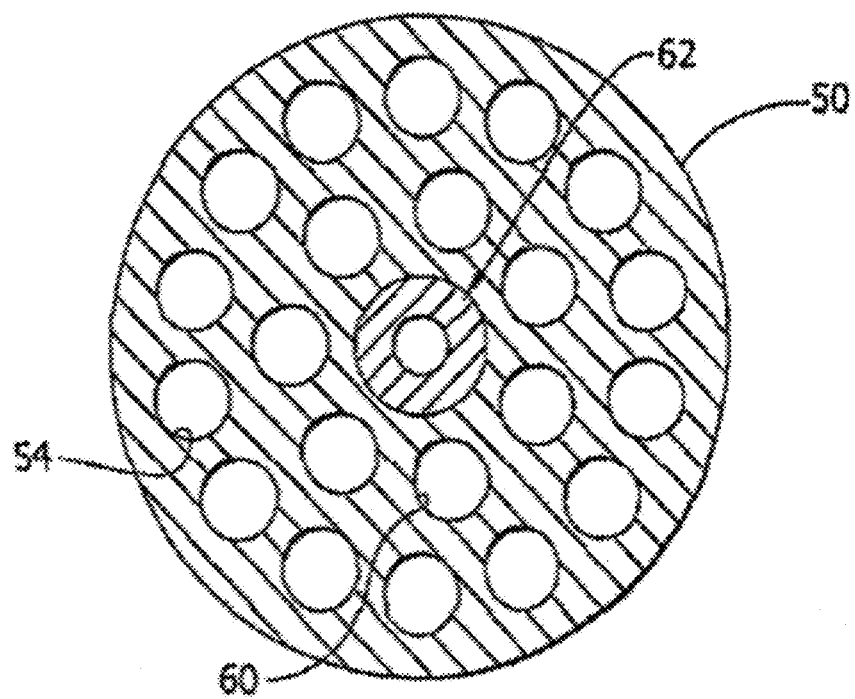

[FIG. 4]
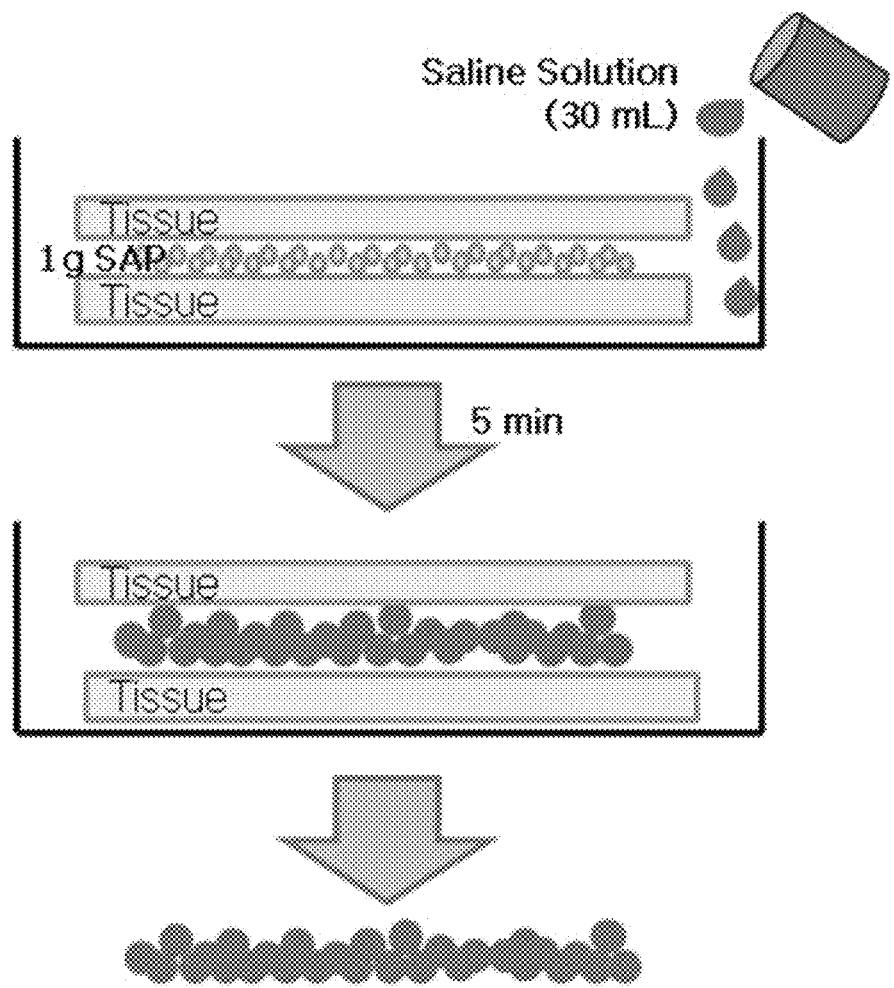

SUPER ABSORBENT POLYMER AND PREPARATION METHOD THEREOF

CROSS-REFERENCE TO RELATED APPLICATIONS

The present application is a national phase entry under 35 U.S.C. § 371 of Internal Application No. PCT/KR2016/015416 filed on Dec. 28, 2016, which claims priority from Korean Patent Application No. 10-2016-0169388 filed on Dec. 13, 2016, the entire contents of which are incorporated herein by reference.

TECHNICAL FIELD

The present invention relates to a super absorbent polymer having reduced 3-hour saline solution re-wet while having high absorption rate and absorption against pulp, and a preparation method thereof.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the content of pulp is reduced or pulp is not used at all is progressing actively.

As described above, in the case of hygienic materials in which the pulp content is reduced or the pulp is not used, the super absorbent polymer is contained in a relatively high ratio, and these super absorbent polymer particles are inevitably contained in multiple layers in the hygienic materials. In order for the whole super absorbent polymer particles contained in the multiple layers to absorb liquid such as urine more efficiently, it is necessary that the super absorbent polymer basically exhibits high absorption performance and absorption rate.

For this purpose, conventional super absorbent polymers use a method of lowering the degree of internal crosslinking and increasing the degree of surface crosslinking. However, in the above method, there is an aspect in which the absorption rate increases, but after the super absorbent resin is swollen by the absorbed liquid, the liquid is present on the surface of the super absorbent polymer, thereby decreasing the wearing feeling and causing skin rashes.

As described above, the degree to which no liquid is present on the surface after the super absorbent polymer has absorbed the liquid is called dryness. Thus, there is a need to develop a super absorbent polymer having excellent dryness without inhibiting the absorption performance and absorption rate of the super absorbent polymer.

DISCLOSURE

Technical Problem

It is one object of the present invention to provide a super absorbent polymer having reduced 3-hour saline solution re-wet while having high absorption rate and absorption against pulp, and a preparation method thereof.

Technical Solution

In order to achieve the above object, there is provided a super absorbent polymer, which comprises:

a base polymer powder containing a first crosslinked polymer of a water-soluble ethylenically unsaturated monomer having an acidic group in which at least a part thereof is neutralized; and a surface crosslinked layer formed on the base polymer powder and containing a second crosslinked polymer in which the first crosslinked polymer is additionally crosslinked via a surface crosslinking agent, wherein the super absorbent polymer has an absorption rate (vortex) of 50 seconds or less, an absorption against pulp of 15 g/g or more, and a 3-hour saline solution re-wet of 1.0 g or less.

As described above, the super absorbent resin according to the present invention has features that it has reduced 3-hour saline solution re-wet while having high absorption rate and absorption against pulp. The super absorbent polymer as described above can be obtained by adjusting the production conditions of the super absorbent polymer as described later.

Hereinafter, the present invention will be described in detail.

Super Absorbent Polymer

The water-soluble ethylenically unsaturated monomer constituting the first crosslinked polymer may be any monomer conventionally used in the production of a super absorbent polymer. As a non-limiting example, the water-soluble ethylenically unsaturated monomer may be a compound represented by the following Chemical Formula 1:

   [Chemical Formula 1]

in Chemical Formula 1, $R_1$ is an alkyl group having 2 to 5 carbon atoms and containing an unsaturated bond, and $M_1$ is a hydrogen atom, a monovalent or divalent metal, an ammonium group or an organic amine salt.

Preferably, the above-mentioned monomer may be at least one selected from the group consisting of acrylic acid, methacrylic acid, and monovalent metal salts, divalent metal salts, ammonium salts, and organic amine salts of these acids. In this way, when acrylic acid or a salt thereof is used as the water-soluble ethylenically unsaturated monomer, it is advantageous because it is possible to obtain a super absorbent polymer having improved water absorbency. In addition, examples of the monomers include maleic anhydride, fumaric acid, crotonic acid, itaconic acid, 2-acryloylethanesulfonic acid, 2-methacryloylethanesulfonic acid, 2-(meth)acryloylpropanesulfonic acid, 2-(meth)acrylamide-2-methylpropane sulfonic acid, (meth)acrylamide, N-substituted (meth)acrylate, 2-hydroxyethyl (meth)acrylate, 2-hydroxypropyl (meth)acrylate, methoxypolyethylene glycol (meth)acrylate, polyethylene glycol (meth)acrylate, (N,N)-dimethylaminoethyl (meth)acrylate, (N,N)-dimethylaminopropyl (meth)acrylamide, and the like.

Here, the water-soluble ethylenically unsaturated monomer has an acidic group, wherein at least a part of the acidic group may be neutralized. Preferably, those that the monomer is partially neutralized with an alkali substance such as sodium hydroxide, potassium hydroxide, ammonium hydroxide or the like can be used.

At this time, the degree of neutralization of the monomer may be 40 to 95 mol %, or 40 to 80 mol %, or 45 to 75 mol %. The range of the degree of neutralization may vary depending on the final physical properties. However, if the degree of neutralization is too high, the neutralized monomers may precipitate and polymerization may not proceed smoothly. Conversely, if the degree of neutralization is too low, not only the absorption capacity of the polymer decreases greatly, but also it can exhibit properties like elastic rubber which is difficult to handle.

The second crosslinked polymer is obtained by additionally crosslinking the surface of the base polymer powder via a surface crosslinking agent, and the surface crosslinking agent and the method of surface crosslinking will be described later.

On the other hand, the super absorbent resin according to the present invention has an absorption rate (vortex) of 50 seconds or less. The above absorption rate means a time during which the vortex of the liquid disappears due to rapid absorption when the super absorbent polymer is added to the physiological saline solution and stirred. This can define the rapid absorption rate of the super absorbent polymer. The method of measuring the absorption rate will be more specified in the following embodiments. Preferably, the absorption rate is 49 seconds or less, 48 seconds or less, 47 seconds or less, 46 seconds or less, or 45 seconds or less. Further, the smaller the value of the absorption rate, it is more excellent. Thus, the lower limit of the absorption rate is theoretically 0 seconds, but for example, 10 seconds or more, 20 seconds or more, 21 seconds or more, 22 seconds or more, 23 seconds or more, 24 seconds or more, or 25 seconds or more.

Further, the super absorbent polymer according to the present invention has an absorption against pulp of 15 g/g or more. The absorption against pulp means the ability of the super absorbent polymer to draw moisture from the pulp. The method of measuring the absorption against pulp will be more specified in the following embodiments. Preferably, the absorption against pulp is 16 g/g or more, 17 g/g or more, 18 g/g or more, 19 g/g or more, or 20 g/g or more. Also, the larger the value of the absorption against pulp, it is more excellent. Thus, although there is no practical upper limit, it is 25 g/g or less, 24 g/g or less, or 23 g/g or less.

Further, the super absorbent polymer according to the present invention has a 3-hour saline solution rewet of 1.0 g or less. The 3-hour saline solution rewet means the amount of moisture oozing out from the super absorbent polymer after the super absorbent polymer is swollen by absorbing a saline solution and then 3 hours lapse, and is associated with a wearing feeling. The method for measuring the 3-hour saline solution re-wet will be more specified in the following embodiments. Preferably, the 3-hour saline solution rewet is 0.9 or less, 0.8 or less, or 0.7 or less. The smaller the value of the 3-hour saline solution rewet, it is more excellent. Thus, the practical lower limit is 0 g, but for example, 0.1 g or more, or 0.2 g or more.

In addition, the super absorbent polymer according to the present invention has an absorbency under pressure at 0.9 psi (0.9 AUP) of 9 g/g or more. The absorbency under pressure means the amount of liquid that can be absorbed in a state where a certain pressure is applied to the super absorbent polymer. The method for measuring the absorbency under pressure will be more specified in the following embodiments. In addition, the higher the value of the 0.9 AUP, it is more excellent. Thus, although there is no practical upper limit, it is for example 20 g/g or less, 19 g/g or less, 18 g/g or less, 17 g/g or less, 16 g/g or less, or 15 g/g or less.

Further, the super absorbent polymer according to the present invention has a centrifuge retention capacity (CRC) of 28 g/g or more. The centrifuge retention capacity means the amount of liquid that can be absorbed by the super absorbent polymer. The method of measuring the centrifuge retention capacity will be more specified in the following embodiments. Preferably, the centrifuge retention capacity is 29 g/g or more, 30 g/g or more, 31 g/g or more, 32 g/g or more, or 33 g/g or more. Further, the higher the value of the centrifuge retention capacity, it is more excellent. Thus, although there is no practical upper limit, it is for example 40 g/g or less, 39 g/g or less, or 38 g/g or less.

Further, the super absorbent polymer according to the present invention has a gel bed permeability (GBP) of 9 Darcy or more. The gel bed permeability means the degree to which the liquid absorbed on the surface of the super absorbent polymer moves to the inside of the super absorbent polymer or other super absorbent polymer. The method of measuring the gel bed permeability is further specified in the following embodiments. The higher the value of the gel bed permeability, it is more excellent. Although there is no theoretical limitation on the upper limit, the gel bed permeability is for example 20 Darcy or less, 19 Darcy or less, 18 Darcy or less, 17 Darcy or less, 16 Darcy or less, or 15 Darcy or less Method for Producing Super Absorbent Polymer The present specification provides a method for preparing a super absorbent polymer comprising the steps of:

crosslinking a water-soluble ethylenically unsaturated monomer having an acidic group in which at least a part thereof is neutralized in the presence of an internal crosslinking agent to form a hydrogel polymer containing a first crosslinked polymer;

drying, pulverizing and classifying the hydrogel polymer to form a base polymer power; and heat-treating and surface-crosslinking the base polymer powder in the presence of a surface crosslinking solution to form a super absorbent polymer particle, wherein the surface crosslinking solution contains a compound having two or more epoxy rings and a compound having two or more hydroxy groups in a weight ratio of 1:0.01 to 1:7.6.

Hereinafter, the above preparation method will be described in detail for each step.

(Step 1)

The step 1 is a step of forming a hydrogel polymer which is a step of crosslinking a monomer composition comprising an internal crosslinking agent and a water-soluble ethylenically unsaturated monomer having an acidic group in which at least a part thereof is neutralized.

The water-soluble ethylenically unsaturated monomer is as described above. Further, the concentration of the water-soluble ethylenically unsaturated monomer in the monomer composition may be appropriately adjusted in consideration of the polymerization time, the reaction conditions and the like, and it may be preferably 20 to 90% by weight, or 40 to 65% by weight. These concentration ranges may be advantageous for adjusting the pulverization efficiency during pulverization of the polymer as described below, without needing to remove unreacted monomers after polymerization by using the phenomenon of gel effect occurring in the polymerization reaction of the highly concentrated aqueous solution. However, when the concentration of the monomer is excessively low, the yield of the super absorbent polymer can be lowered. Conversely, when the concentration of the monomer is excessively high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

As an internal crosslinking agent, any compound can be used without particular limitation as long as it enables introduction of a crosslinking bond upon polymerization of the water-soluble ethylenically unsaturated monomer. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triallylamine, ethylene glycol diglycidyl ether, propylene glycol, glycerin, or ethylene carbonate, which may be used alone or in combination of two or more thereof, but are not limited thereto. Preferably, two kinds of polyethylene glycol diacrylates having different molecular weights are used.

Such internal crosslinking agent may be added at a concentration of about 0.001% by weight to 1% by weight, based on the monomer composition. That is, if the concentration of the internal crosslinking agent is too low, the absorption rate of the polymer is lowered and the gel strength may become weak, which is undesirable. Conversely, if the concentration of the internal crosslinking agent is too high, the absorption capacity of the polymer is lowered and thereby is not preferred for an absorbent.

Further, in the step 1, a polymerization initiator generally used in the production of a super absorbent polymer can be included. As a non-limiting example, as the polymerization initiator, a thermal polymerization initiator, a photo-polymerization initiator or the like may be used depending on the polymerization method. In particular, the thermal polymerization initiator can be used. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

As the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4$)$_2S_2O_8$), and the like. In addition, examples of the azo-based initiator may include 2,2-azobis(2-amidinopropane)dihydrochloride, 2,2-azobis-(N,N-dimethylene) isobutyramidine dihydrochloride), 2-(2-(carbamoylazo) isobutylonitril), 2,2-azobis[2-(2-imidazolin-2-yl)propane] dihydrochloride), (4,4-azobis-(4-cyanovaleric acid), and the like. More various thermal polymerization initiators are well disclosed in "Principle of Polymerization" written by Odian, (Wiley, 1981), p 203, the content of which is incorporated herein by reference. Preferably, ascorbic add and potassium persulfate are used as the thermal polymerization initiator.

The photo-polymerization initiator used herein may include, for example, one or more compounds selected from the group consisting of benzoin ether, dialkyl acetophenone, hydroxyl alkylketone, phenyl glyoxylate, benzyl dimethyl ketal, acyl phosphine and α-aminoketone. Among them, as a specific example of the acylphosphine, a commonly used lucyrin TPO, that is, 2,4,6-trimethyl-benzoyl-trimethyl phosphine oxide may be used. More various photo-polymerization initiators are well disclosed in "UV Coatings: Basics, Recent Developments and New Application" written by Reinhold Schwalm, (Elsevier, 2007), p 115, the content of which is incorporated herein by reference.

The polymerization initiator may be added in a concentration of about 0.001% to 1% by weight based on the monomer composition. That is, when the concentration of the polymerization initiator is too low, the polymerization rate may become slow and a large amount of residual monomer may be extracted in the final product, which is not preferable. Conversely, when the concentration of the polymerization initiator is higher than the above range, the polymer chains constituting the network become short, and thus the extractable content is increased and physical properties of the polymer may deteriorate such as a reduction in absorbency under pressure, which is not preferable.

In addition, the monomer composition may further include additives such as a surfactant, a thickener, a plasticizer, a preservation stabilizer, an antioxidant, etc., if necessary.

Further, such a monomer composition can be prepared in the form of a solution in which a raw material such as the above-mentioned monomer is dissolved in a solvent. In this case, any usable solvent can be used without limitation in the constitution as long as it can dissolve the above-mentioned raw material. Examples of the solvent may include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

Further, the formation of the hydrogel polymer through polymerization of the monomer composition may be performed by a general polymerization method, and the process is not particularly limited. Non-limiting examples of the polymerization method are largely classified into a thermal polymerization and a photo-polymerization according to the type of the polymerization energy source, and the thermal polymerization may be carried out in a reactor like a kneader equipped with agitating spindles and the photo-polymerization may be carried out in a reactor equipped with a movable conveyor belt.

For example, the monomer composition is injected into a reactor like a kneader equipped with the agitating spindles, and thermal polymerization is performed by providing hot air thereto or heating the reactor, thereby obtaining the hydrogel polymer. In this case, the hydrogel polymer, which is discharged from the outlet of the reactor according to the type of agitating spindles equipped in the reactor, may be obtained as particles with a size of centimeters or millimeters. Specifically, the hydrogel polymer may be obtained in various forms according to the concentration of the monomer composition injected thereto, the injection speed, or the like, and the hydrogel polymer having a (weight average) particle diameter of 2 mm to 50 mm may be generally obtained.

As another example, when the photo-polymerization of the monomer composition is performed in a reactor equipped with a movable conveyor belt, a sheet-shaped hydrogel polymer may be obtained. In this case, the thickness of the sheet may vary depending on the concentration of the monomer composition injected thereto and the injection speed, and the polymer sheet is preferably controlled to have typically a thickness of 0.5 to 10 cm in order to secure the production speed or the like while uniformly polymerizing the entire sheet.

The hydrogel polymer formed by the above-mentioned method may have a water content of about 40 to 80% by weight. Meanwhile, the "water content" as used herein means a weight occupied by moisture with respect to a total weight of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the drying conditions may be determined as follows: the drying temperature is increased from room temperature to about 180° C. and then the temperature may be maintained at 180° C., and the total drying time may be set to 20 minutes, including 5 minutes for the temperature rising step.

(Step 2)

The step 2 is a step of drying, pulverizing and classifying the hydrogel polymer to form a base polymer power. The base polymer powder, and the super absorbent polymer obtained therefrom are suitably manufactured and provided so as to have a particle diameter of about 150 μm to 850 μm. More specifically, at least about 95% by weight or more of the base polymer powder and the super absorbent polymer obtained therefrom has a particle diameter of about 150 μm to 850 μm and the fine particles having a particle diameter of less than about 150 μm can be less than about 3% by weight. As such, as the particle diameter distribution of the base polymer powder and the super absorbent polymer is adjusted to the preferable range, the super absorbent polymer finally produced can better exhibit the above-mentioned physical properties.

On the other hand, the method of drying, pulverization and classification will be described in more detail below.

First, when drying the hydrogel polymer, a coarsely pulverizing step may be further carried out before drying in order to increase the efficiency of the drying step, if necessary. A pulverizing machine used herein may include, but its configuration is not limited to, for example, any one selected from the group consisting of a vertical pulverizing device, a turbo cutter, a turbo grinder, a rotary cutter mill, a cutter mill, a disc mill, a shred crusher, a crusher, a chopper, and a disc cutter. However, it is not limited to the above-described examples.

In this case, the coarsely pulverizing step may be carried out so that the particle diameter of the hydrogel polymer becomes about 2 mm to about 10 mm. Pulverizing the hydrogel polymer into a particle diameter of less than 2 mm is technically not easy due to its high moisture content, and agglomeration may occur between the pulverized particles. Meanwhile, if the polymer is pulverized into a particle diameter of greater than 10 mm, the effect of increasing the efficiency in the subsequent drying step may be insignificant.

The hydrogel polymer coarsely pulverized as above or the hydrogel polymer immediately after polymerization without the coarsely pulverizing step is subjected to a drying step. In this case, the drying temperature of the drying step may be about 50° C. to about 250° C. When the drying temperature is less than 50° C., it is likely that the drying time becomes too long and the physical properties of the super absorbent polymer finally formed is deteriorated, and when the drying temperature is higher than 250° C., only the surface of the polymer is excessively dried, and thus it is likely that fine powder may be generated during the subsequent pulverizing step and the physical properties of the super absorbent polymer finally formed is deteriorated. The drying may be carried out preferably at a temperature of about 150° C. to about 200° C., more preferably 160° C. to about 190° C. Meanwhile, the drying time may be about 20 minutes to 15 hours, in consideration of the process efficiency and the like, but it is not limited thereto.

The drying method may also be selected and used without any limitation if it is a method generally used for drying the hydrogel polymer. Specifically, the drying step may be carried out by a method such as hot air supply, infrared irradiation, microwave irradiation or ultraviolet irradiation. The moisture content of the polymer after such a drying step may be about 0.05% to about 10% by weight.

Next, a step of pulverizing the dried polymer obtained through such a drying step is carried out.

The polymer powder obtained through the pulverizing step may have a particle diameter of about 150 μm to about 850 μm. Specific examples of a pulverizing device that can be used to perform pulverization with the above particle diameter may include a ball mill, a pin mill, a hammer mill, a screw mill, a roll mill, a disc mill, a jog mill or the like, but it is not limited thereto.

Also, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of about 150 μm to about 850 μm is classified and only the polymer powder having such a particle diameter is subjected to the surface crosslinking reaction and finally commercialized.

(Step 3)

The step 3 is a step of crosslinking the surface of the base resin polymer, which is a step heat-treating and surface-crosslinking the base polymer powder in the presence of a surface crosslinking solution to form a super absorbent polymer particle.

Particularly, in the present invention, as a surface crosslinking agent contained in the surface crosslinking solution, a compound having two or more epoxy rings and a compound having two or more hydroxy groups is used in a weight ratio of 1:0.01 to 1:7.6. If it is out of the above range, appropriate surface crosslinking will not proceed and thus the physical properties of the super absorbent polymer required in the present invention cannot be satisfied. Preferably, the weight ratio is 1:1 to 1:3.

Examples of the compound having two or more epoxy rings include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, 1,4-butanediol diglycidyl ether, 1,4-cyclohexanedimethanol diglycidyl ether, hexahydrophthalic anhydride diglycidyl ether, neopentyl glycol diglycidyl ether, bisphenol A diglycidyl ether, and N,N-diglycidylaniline. Preferably, ethylene glycol diglycidyl ether is used.

Further, examples of the compound having two or more hydroxy groups include one or more compounds selected from the group consisting of ethylene glycol, diethylene glycol, propylene glycol, triethylene glycol, tetraethylene glycol, propane diol, dipropylene glycol, polypropylene glycol, glycerin, polyglycerin, butane diol, heptane diol, hexane diol, trimethylol propane, pentaerythritol, and sorbitol. Preferably, propylene glycol is used.

As the content of the surface crosslinking agent based on the compound having two or more epoxy rings, the compound having two or more epoxy rings is preferably used in an amount of 0.01 to 0.5 parts by weight, relative to 100 parts by weight of the base polymer. When the content of the surface crosslinking agent exceeds 0.5 parts by weight, excessive surface crosslinking proceeds, and when the water-absorbent resin absorbs water, a large amount of water is present on the surface, thereby lowering the dryness and the 3-hour saline solution re-wet. Conversely, when the content of the surface crosslinking agent is less than 0.01 part by weight, sufficient surface crosslinking does not proceed and various physical properties of the super absorbent polymer are deteriorated.

Further, the surface crosslinking solution contains water, and the content of water is 0.5 to 10 parts by weight based on 100 parts by weight of the base polymer powder.

Further, the surface crosslinking solution may contain aluminum sulfate. The aluminum sulfate may be contained in an amount of 0.01 to 0.5 parts by weight based on 100 parts by weight of the base polymer powder.

Further, the surface crosslinking solution may contain an inorganic filler. The inorganic filler may include silica, aluminum oxide, or silicate. The inorganic filler may be contained in an amount of 0.01 to 0.5 parts by weight based on 100 parts by weight of the base polymer powder.

Further, the surface crosslinking solution may contain a thickener. If the surface of the base polymer powder is further crosslinked in the presence of the thickener, it is possible to minimize the deterioration of the physical properties even after the pulverization. Specifically, as the thickener, at least one selected from a polysaccharide and a hydroxy-containing polymer may be used. The polysaccharide may be a gum type thickener, a cellulose type thickener and the like. Specific examples of the gum type thickener include xanthan gum, arabic gum, karaya gum, tragacanth gum, Bhatti gum, guar gum, guar gum, locust bean gum, and psyllium seed gum. Specific examples of the cellulose type thickener include hydroxypropylmethyl cellulose, carboxymethyl cellulose, methylcellulose, hydroxymethyl cellulose, hydroxyethyl cellulose, hydroxypropyl cellulose, hydroxyethylmethyl cellulose, hydroxymethylpropyl cellulose, hydroxyethylhydroxypropyl cellulose, ethylhydroxyethyl cellulose, and methylhydroxypropyl cellulose. Meanwhile, specific examples of the hydroxy-containing polymer include polyethylene glycol, polyvinyl alcohol and the like.

On the other hand, in order to perform the surface crosslinking, a method of placing the surface crosslinking solution and the base polymer into a reaction tank and mixing them, a method of spraying a surface crosslinking solution onto the base polymer, a method in which the base polymer and the surface crosslinking solution are continuously supplied in a continuously operating mixer and mixed, or the like can be used.

In addition, the surface crosslinking may be carried out at a temperature of 100 to 250° C., and may be continuously performed after the drying and pulverizing step proceeding at a relatively high temperature. At this time, the surface crosslinking reaction may be carried out for 1 to 120 minutes, or 1 to 100 minutes, or 10 to 60 minutes. That is, it can be performed under the condition of the surface crosslinking reaction described above in order to prevent the polymer particles from being damaged and the physical properties thereof from being decreased.

Advantageous Effects

As described above, the super absorbent polymer according to the present invention has reduced 3-hour saline solution re-wet while having a high absorption rate and absorption against pulp, and thus can be used for hygienic materials such as diapers, thereby exhibiting excellent performance.

BRIEF DESCRIPTION OF THE DRAWINGS

FIG. 1 is a schematic view showing an example of an apparatus for measuring a gel bed permeability (GBP) according to an embodiment of the present invention.

FIGS. 2 and 3 are schematic views showing an example of a chamber and a mesh arrangement for measuring the gel bed permeability, respectively.

FIG. 4 schematically shows a method of measuring an absorption against pulp according to an embodiment of the present invention.

DETAILED DESCRIPTION OF THE EMBODIMENTS

Hereinafter, preferred embodiments are presented to facilitate understanding of the invention. However, the following examples are for illustrative purposes only and are not intended to limit the scope of the present invention thereto.

Example 1

A solution in which 20.5 g (80 ppm) of 0.21% IRGACURE 819 initiator diluted with 500 g of acrylic acid was mixed, and a solution in which 21 g of 10% polyethylene glycol diacrylate (PEGDA, Mw=400) diluted with acrylic acid was mixed were injected. Then, 12 g of 2% SDS (sodium dodecyl sulfate) solution was mixed therein, to which 800 g of a 24% caustic soda solution was slowly added dropwise and mixed. The water-soluble ethylenically unsaturated monomer was thus obtained, and the degree of neutralization of acrylic acid in the sodium acrylate was 70 mol %.

When mixing the two solutions, it was confirmed that the temperature of the mixture was increased by 72° C. or more by neutralizing heat. Then, when the temperature was cooled to 43° C., 13.4 g of a 4% sodium bicarbonate solution was mixed, and at the same time, 16 g of 4% sodium persulfate solution diluted with water was injected.

Then, the above prepared solution was poured in a tray (15 cm in width×15 cm in length) installed in a square polymerizer which had a UV irradiation device installed at the top and whose inside was preheated to 80° C. Polymerization was initiated by irradiating an ultraviolet ray. The sheet-shaped polymer produced was cut into a size of about 5 cm×5 cm, and then put into a meat chopper to pulverize the polymer, thereby obtaining hydrogel particles having a size of 1 mm to 10 mm.

The crumps were dried in an oven capable of shifting airflow upward and downward. The crumbs were uniformly dried by flowing hot air at 180° C. from the bottom to the top for 15 minutes and again from the top to the bottom for 15 minutes, and thereby a water content of the dried product was set to 2% or less. After drying, the dried product was pulverized using a pulverizing device and classified into a size of 150 to 850 μm to obtain a base polymer.

4 g of water, 4 g of methanol, 0.25 g of EX-810 (Ethylene Glycol Diglycidyl Ether), 0.3 g of propylene glycol (PG), 0.15 g of aluminum sulfate (Al—S), 0.1 g of fumed silica (AEROXIDE® Alu 130), and 0.05 g of a reducing agent ($Na_2S_2O_5$) were mixed to prepare a crosslinking agent solution. The surface crosslinking agent solution was mixed with 100 g of the base polymer powder obtained above, and the mixture was placed in a convection oven at 140° C. and allowed to react for 35 minutes. The produced powder was classified with a standard mesh sieve according to ASTM standard to obtain a super absorbent polymer having a particle size of 150 to 850 μm.

Examples 2-5 and Comparative Examples 1-4

The super absorbent polymer was prepared in the same manner as in Example 1, except that the composition of the surface crosslinking agent solution was changed as shown in Table 1 below.

Experimental Example

Evaluation of Physical Properties of Super Absorbent Polymer

The physical properties of the super absorbent polymer prepared in the above Examples and Comparative Examples were evaluated by the following methods.

(1) Centrifuge Retention Capacity (CRC)

The centrifuge retention capacity(CRC) by water absorption capacity under a non-loading condition was measured for the super absorbent polymers of Examples and Comparative Examples in accordance with EDANA (European Disposables and Nonwovens Association) recommended test method No. WSP 241.3.

Specifically, $W_0(g)$ (about 0.2 g) of the super absorbent polymers of Examples and Comparative Examples were uniformly put in a nonwoven fabric-made bag, followed by sealing. Then, the bag was immersed in a physiological saline solution composed of 0.9 wt % aqueous sodium chloride solution at room temperature. After 30 minutes, water was removed from the bag by centrifugation at 250 G for 3 minutes, and the weight $W_2(g)$ of the bag was then measured. Further, the same procedure was carried out without using the super absorbent polymer, and then the resultant weight $W_1(g)$ was measured.

Using the respective weights thus obtained, CRC (g/g) was calculated according to the following Mathematical Formula 1.

$$CRC(g/g) = \{[W_2(g) - W_1(g) - W_0(g)]/W_0(g)\} \quad \text{[Mathematical Formula 1]}$$

in Mathematical Formula 1, $W_0(g)$ is an initial weight(g) of the super absorbent polymer, $W_1(g)$ is the weight of the device not including the super absorbent polymer, measured after dehydrating the same by using a centrifuge at 250 G for 3 minutes, and $W_2(g)$ is the weight of the device including the super absorbent polymer, measured after immersing and absorbing the super absorbent polymer into a physiological saline solution at room temperature for 30 minutes and then dehydrating the same by using a centrifuge at 250 G for 3 minutes.

(2) 3-Hour Saline Solution Re-Wet 2 g of the super absorbent polymer prepared in the above Examples and Comparative Examples was placed in a 500 mL beaker, and 60 mL of 0.9 wt % sodium chloride aqueous solution was added thereto at room temperature (about 22 to 24° C.) was added thereto and kept for 3 hours. Then, five sheets of filter papers with a diameter of 5 cm were stacked on the swollen super absorbent polymer, and a piston capable of uniformly applying a load of 0.2 psi was placed on the filter paper. After 1 minute, the weight of aqueous sodium chloride solution absorbed by the filter paper (3-hour saline solution re-wet) was measured.

(3) Absorption Rate (Vortex)

50 mL of a 0.9 wt % sodium chloride aqueous solution was placed in a 100 mL beaker and 2 g of the super absorbent polymers prepared in the Examples and Comparative Examples were each added thereto while stirring at 600 rpm using a stirrer. Then, the amount of time until the vortex of the liquid caused by the stirring disappeared and a smooth surface was formed was measured, and the result was expressed by the vortex removal time (absorption rate; vortex).

(4) Absorbency Under Pressure (AUP)

The absorbency under Pressure (AUP) was measured for the super absorbent polymers of the Examples and Comparative Examples in accordance with EDANA (European Disposables and Nonwovens Association) recommended test method No. WSP 242.3.

Specifically, a 400 mesh stainless steel net was installed in the bottom of a plastic cylinder having an internal diameter of 60 mm. The absorbent polymers $W_0(g)$ (about 0.90 g) obtained in the Examples and Comparative Examples were uniformly scattered on the steel net under conditions of temperature of 23±2° C. and relative humidity of 45%, and a piston which can provide a load of 0.9 psi uniformly was put thereon. The external diameter of the piston was slightly smaller than 60 mm, there was no gap between the internal wall of the cylinder and the piston, and the jig-jog of the cylinder was not interrupted. In this case, the weight $W_3(g)$ of the device was measured.

After putting a glass filter having a diameter of 125 mm and a thickness of 5 mm in a Petri dish having a diameter of 150 mm, a physiological saline solution composed of 0.90 wt % sodium chloride was poured in the dish until the surface level became equal to the upper surface of the glass filter. A sheet of filter paper having a diameter of 120 mm was put thereon. The measuring device was put on the filter paper and the solution was absorbed under a load for about 1 hour. After 1 hour, the weight $W_4(g)$ was measured after lifting the measuring device up.

Using the respective weights thus obtained, the AUP (g/g) was calculated according to the following Mathematical Formula 2.

$$AUP(g/g) = [W_4(g) - W_3(g)]/W_0(g) \quad \text{[Mathematical Formula 2]}$$

in Mathematical Formula 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.9 psi) for 1 hour.

(5) Gel Bed Permeability (GBP)

The gel bed permeability (GBP) was measured for the super absorbent polymer prepared in the Examples and the Comparative Examples. The measurement method of GBP is disclosed in in U.S. Pat. No. 7,179,851.

First, the apparatus suitable for carrying out the gel bed permeability test is shown in FIG. 1. The test apparatus 28 comprises a sample container, generally indicated at 30, and a piston, generally indicated at 35. The piston 35 comprises a cylindrical LEXAN shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 comprises a cylinder 34 and a 400 mesh stainless steel cloth screen 66 that is biaxially stretched to tautness and attached to the lower end of the cylinder. A gel particle sample, indicated as 68 in FIG. 3, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of about 10 cm. Drainage holes (not shown) are formed in the sidewall of the cylinder 34 at a height of about 7.8 cm above the screen 66 to allow liquid to drain from the cylinder to thereby maintain a fluid level in the sample container at approximately 7.8 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 wt % sodium chloride solution in distilled water. The combined weight of the piston 35 and annular weight 48 equals approximately 596 g, which corresponds to a pressure applied to the sample 68 of about 0.3 psi, or about 20.7 g/cm$^2$, over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the gel bed permeability test under "free swell" conditions, the piston 35, with the weight 48 seated thereon, is placed in an empty sample container 30 and the height is measured using a suitable gauge accurate to 0.01 mm with the platen removed. It is important to measure the height of each sample container 30 empty and to keep track of which piston 35 and weight 48 is used when using multiple test apparatus. The same piston 36 and weight 48 should be used for measurement when the sample 68 is later swollen following saturation.

The sample to be tested is prepared from super absorbent material particles which are prescreened through a U.S. standard 30 mesh screen and retained on a U.S. standard 50 mesh screen. As a result, the test sample comprises particles sized in the range of about 300 to about 600 µm. The particles can be prescreened by hand or automatically. About 2.0 g of the sample is placed in the sample container 30, and the container, without the piston 35 and weight 48 therein, is then submerged in the test solution for a time period of about 60 minutes to saturate the sample and allow the sample to swell free of any restraining load.

At the end of this period, the piston 35 and weight 48 assembly is placed on the saturated sample 68 in the sample container 30 and then the sample container 30, piston 35, weight 48, and sample 68 are removed from the solution. The thickness of the saturated sample 68 is determined by again measuring the height from the bottom of the weight 48 to the top of the cylinder 34, using the same clipper or gauge used previously, provided that the zero point is unchanged from the initial height measurement. The height measurement value obtained from measuring the empty sample container 30, piston 35, and weight 48 is subtracted from the height measurement value obtained after saturating the sample 48. The resulting value is the thickness, or height "H" of the swollen sample.

The permeability measurement is initiated by delivering a flow of the test solution into the sample container 30 with the saturated sample 68, piston 35, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least 20 seconds once the fluid level has been stabilized to and maintained at about 7.8 cm in height. The flow rate Q through the swollen sample 68 is determined in units of grams/second (g/s) by a linear least-square fit of fluid passing through the sample 68 (in grams) versus time (in seconds).

Permeability in Darcy is obtained by the following Mathematical Formula 3.

$$K=[Q \times H \times Mu]/[A \times Rho \times P] \qquad \text{[Mathematical Formula 3]}$$

in Mathematical Formula 3, K is a permeability (cm$^2$), Q is a flow rate (g/sec), H is a height of sample (cm), Mu is a liquid viscosity (poise) (approximately one centipoises for the test solution used with this Test), A is a cross-sectional area for liquid flow (cm$^2$), Rho is a liquid density (g/cm$^3$) (for the test solution used with this Test) and P is a hydrostatic pressure (dynes/cm$^2$) (normally approximately 3,923 dynes/cm$^2$). The hydrostatic pressure is calculated by the following Mathematical Formula 4.

$$P = Rho \times g \times h \quad \text{[Mathematical Formula 4]}$$

in Mathematical Formula 4, Rho is a liquid density (g/cm$^3$), g is a gravitational acceleration, nominally 981 cm/sec$^2$, and h is a fluid height, e.g., 7.8 cm for the Gel Bed Permeability Test described herein.

(6) AAP (Absorption Against Pulp, Ability to Absorb Moisture from Pulp)

The ability to absorb moisture from the pulp (AAP) was measured by the method as shown in FIG. 4. Specifically, 6 sheets of tissues with a size of 107 mm×107 mm tissue (Kimberly Kimtec Science Wipers, small size) were placed in plastic disposable dish with a size of 140 mm×140 mm. 1 g of the super absorbent polymer prepared in the Examples and Comparative Examples was uniformly sprayed as a whole on the tissue, and then six sheets of tissues were placed thereon. 30 mL of 0.9% sodium chloride aqueous solution was poured onto the tissue and swollen for 5 minutes, and then the weight (AAP) of the swollen gel between the tissues was measured.

The above measurement results are shown in Table 1 below.

TABLE 1

| | Composition of surface crosslinking solution | | | | | Saline solution re-wet | | | | Physical property of super absorbent polymer |
|---|---|---|---|---|---|---|---|---|---|---|
| Unit | EX-810 g | PG g | Al—S g | Silica g | CRC g/g | wet g | Vortex sec | 0.9 AUL g/g | GBP darcy | AAP g/g |
| Ex. 1 | 0.25 | 0.3 | 0.15 | 0.1 | 34.0 | 0.3 | 32 | 10 | 11 | 22 |
| Ex. 2 | 0.25 | 0.3 | 0.20 | 0.02 | 35.2 | 0.5 | 40 | 10 | 9 | 19 |
| Ex. 3 | 0.25 | 0.6 | 0.15 | 0.1 | 33.8 | 0.3 | 31 | 11 | 10 | 21 |
| Ex. 4 | 0.25 | 0.6 | 0.20 | 0.02 | 34.7 | 0.6 | 42 | 10 | 9 | 18 |
| Ex. 5 | 0.25 | 1.0 | 0.15 | 0.1 | 32.0 | 0.7 | 30 | 13 | 16 | 18 |
| Comparative Ex. 1 | 0 | 0 | 0.15 | 0.1 | 38.5 | 3.0 | 31 | 9 | 1 | — |
| Comparative Ex. 2 | 0 | 0.25 | 0.15 | 0.1 | 38.5 | 3.1 | 30 | 7 | 1 | 17 |
| Comparative Ex. 3 | 0.1 | 0 | 0.20 | 0.03 | 32.2 | 1.1 | 36 | 11 | 31 | 18 |
| Comparative Ex. 4 | 0.1 | 0 | 0.45 | 0.03 | 34.3 | 1.1 | 33 | 10 | 23 | 17 |
| Comparative Ex. 5 | 0.25 | 2.0 | 0.15 | 0.1 | 30.0 | 2.7 | 33 | 15 | 23 | 16 |

The invention claimed is:

1. A super absorbent polymer comprising:
   a base polymer powder containing a first crosslinked polymer of a water-soluble ethylenically unsaturated monomer having an acidic group in which at least a part thereof is neutralized; and
   a surface crosslinked layer formed on the base polymer powder and containing a second crosslinked polymer in which the first crosslinked polymer is additionally cross-linked via a surface crosslinking solution comprising a compound having two or more epoxy rings and a compound having two or more hydroxy groups in a weight ratio of 1:1 to 1:4, and water in an amount of 4 to 10 parts by weight based on 100 parts by weight of the base polymer powder,
   wherein the compound having two or more epoxy rings is ethylene glycol diglycidyl ether, and the compound having two or more hydroxy groups is propylene glycol, and
   wherein the super absorbent polymer has an absorption rate (vortex) of 50 seconds or less,
   an absorption against pulp of 18 g/g or more,
   a gel bed permeability (GBP) of 9 Darcy or more, and
   a 3-hour saline solution re-wet of 1.0 g or less.

2. The super absorbent polymer of claim 1, wherein it has an absorption rate (vortex) of 45 seconds or less.

3. The super absorbent polymer of claim 1, wherein it has an absorbency under pressure at 0.9 psi (0.9 AUP) of 9 g/g or more.

4. The super absorbent polymer of claim 1, wherein it has a centrifuge retention capacity (CRC) of 28 g/g or more.

5. A method for preparing the super absorbent polymer of claim 1, the method comprising the steps of:
   crosslinking the water-soluble ethylenically unsaturated monomer having an acidic group in which at least a part thereof is neutralized in the presence of an internal crosslinking agent to form a hydrogel polymer containing the first crosslinked polymer;
   drying, pulverizing and classifying the hydrogel polymer to form e base polymer power, and
   heat-treating and surface-crosslinking the base polymer powder in the presence of the surface crosslinking solution to form a super absorbent polymer particle.

6. The method for preparing a super absorbent polymer of claim 5, wherein the surface crosslinking solution comprises aluminum sulfate.

7. The method for preparing a super absorbent polymer of claim 5, wherein the surface crosslinking solution comprises an inorganic filler.

* * * * *